(12) United States Patent
Lui (10) Patent No.: US 9,959,739 B1
(45) Date of Patent: May 1, 2018

(54) SYSTEM, METHOD AND ARTICLE FOR INDICATING A WET OR DRY CONDITION TO A USER

(71) Applicant: Nantin Enterprise Limited, Hong Kong (HK)

(72) Inventor: Ming Wah Lui, Hong Kong (HK)

(73) Assignee: Nantin Enterprise Limited, Hong Kong (HK)

( * ) Notice: Subject to any disclaimer, the term of this patent is extended or adjusted under 35 U.S.C. 154(b) by 0 days. days.

(21) Appl. No.: 15/338,318

(22) Filed: Oct. 28, 2016

(51) Int. Cl.
G08B 21/00 (2006.01)
G08B 21/20 (2006.01)
G06K 7/10 (2006.01)

(52) U.S. Cl.
CPC ......... *G08B 21/20* (2013.01); *G06K 7/10366* (2013.01)

(58) Field of Classification Search
None
See application file for complete search history.

(56) References Cited

U.S. PATENT DOCUMENTS

| | | | | |
|---|---|---|---|---|
| 4,977,906 A | * | 12/1990 | Di Scipio | A61F 5/48 128/885 |
| 5,790,036 A | * | 8/1998 | Fisher | A61F 13/42 128/886 |
| 6,025,780 A | * | 2/2000 | Bowers | G06K 19/0701 340/10.51 |
| 8,502,684 B2 | * | 8/2013 | Bunza | A61B 5/202 340/572.1 |
| 8,978,452 B2 | * | 3/2015 | Johnson | G01N 27/223 340/604 |
| 2002/0145525 A1 | * | 10/2002 | Friedman | A61B 5/0002 340/573.5 |
| 2005/0242950 A1 | * | 11/2005 | Lindsay | G06K 19/0717 340/539.26 |
| 2006/0111632 A1 | * | 5/2006 | Chen | A61F 2/12 600/431 |

(Continued)

FOREIGN PATENT DOCUMENTS

| | | |
|---|---|---|
| CN | 102324171 A | 1/2012 |
| CN | 103845156 A | 6/2014 |
| CN | 203894918 U | 10/2014 |

OTHER PUBLICATIONS

Search Report issued by the Chinese Patent Office dated Mar. 5, 2016.

*Primary Examiner* — Quan-Zhen Wang
*Assistant Examiner* — Chico A Foxx (57) ABSTRACT

Disclosed is a system, method and an article for indicating wet/dry condition to a user. At least one sensor comprising a circuit of a processing unit, a switch and an antenna is positioned within a target area. The switch detects the target area with a dry condition or a wet condition. The switch arranges the circuit in an open circuit configuration or a closed circuit configuration based upon the detection of the dry condition or the wet condition respectively. The antenna transmits a communication signal, generated by the processing unit, to a wireless reader via the circuit arranged in the open circuit configuration or the closed circuit configuration. The wireless reader determines the dry condition or the wet condition in the target area based upon the receipt of the communication signal. The wireless reader notifies to a user the dry condition or the wet condition detected in the target area.

5 Claims, 5 Drawing Sheets

(56) References Cited

U.S. PATENT DOCUMENTS

| | | | |
|---|---|---|---|
| 2006/0192762 A1* | 8/2006 | Corrion | G06F 3/0317 345/166 |
| 2007/0090927 A1* | 4/2007 | Potyrailo | G06K 19/0717 340/10.41 |
| 2007/0152829 A1* | 7/2007 | Lindsay | G06K 19/0717 340/572.3 |
| 2008/0094226 A1* | 4/2008 | O'Shea | A61B 5/0002 340/573.1 |
| 2008/0110984 A1* | 5/2008 | Uchitani | A61F 13/15804 235/385 |
| 2008/0218731 A1* | 9/2008 | Duesbury | G01N 21/78 356/36 |
| 2010/0123583 A1* | 5/2010 | Bommer | G06K 19/0717 340/572.7 |
| 2012/0206265 A1* | 8/2012 | Solazzo | A61F 13/42 340/573.5 |
| 2013/0036802 A1* | 2/2013 | Johnson | G01N 27/223 73/74 |
| 2013/0162402 A1* | 6/2013 | Amann | G01K 1/024 340/10.1 |
| 2014/0014716 A1* | 1/2014 | Joyce | A61F 13/42 235/375 |
| 2014/0015644 A1* | 1/2014 | Amann | A61F 13/84 340/10.1 |
| 2014/0152442 A1 | 6/2014 | Li | |
| 2014/0198203 A1* | 7/2014 | Vardi | G08B 21/20 348/135 |
| 2014/0358099 A1* | 12/2014 | Durgin | A61F 13/42 604/361 |
| 2015/0080819 A1 | 3/2015 | Charna et al. | |
| 2015/0320609 A1* | 11/2015 | Thoen | G01N 27/048 340/573.5 |
| 2017/0035593 A1* | 2/2017 | Chen | A61F 5/0033 |

\* cited by examiner

SYSTEM, METHOD AND ARTICLE FOR INDICATING A WET OR DRY CONDITION TO A USER

TECHNICAL FIELD

The present application described herein, in general, relates to a system, method and an article for indicating a wet or dry condition to a user, and more particularly, for indicating the wet or dry condition for an absorbent article such as diaper.

BACKGROUND

Absorbent articles such as diapers are being widely used by children and adults in need. Diaper rash is most commonly observed problem today due to frequent wetting and wearing of such wet diapers for prolonged period. There is possibility of skin allergy or urine infection due to frequent bed wetting. Therefore, the wet diapers must be replaced immediately for the purpose of providing hygiene and comfort to an individual wearing the diaper. One of the most effective and preventive measure for avoiding the diaper rash, skin allergy and urine infection is to frequently monitor and check the wet conditions in the diaper and thereby replacing the diaper with wet conditions. However, such manual monitoring and checking of the diaper conditions is onerous and time consuming.

An electronic wet/dry condition detection system has been proposed in the art wherein RFID based sensing circuits are employed to detect the wet/dry conditions within the diapers. However, the RFID based circuits are clumsy in design requiring additional circuits for detection and incorporating multiple sensor wires in order to meet the requirements of the tailor made diapers. Further, the sensors employed in these RFID circuits are not reusable.

SUMMARY

This summary is provided to introduce concepts related to systems, methods and articles for indicating a wet or dry condition to a user and the concepts are further described below in the detailed description. This summary is not intended to identify essential features of the claimed subject matter nor is it intended for use in determining or limiting the scope of the claimed subject matter.

In one implementation, a system for indicating a wet or dry condition to a user is disclosed. The system may comprise at least one sensor positioned within a target area. The at least one sensor may comprise a circuit of a processing unit, a switch and an antenna. The switch may be configured to detect the target area with a dry condition or a wet condition. Further, the switch may be configured to arrange the circuit in an open circuit configuration or a closed circuit configuration based upon the detection of the dry condition and the wet condition respectively. Further, the antenna may be configured to transmit a communication signal, generated by the processing unit, via the circuit arranged in either of the open circuit configuration or the closed circuit configuration. The system may further comprise a wireless reader configured to receive the communication signal from the antenna. The wireless reader may further be configured to determine the dry condition or the wet condition in the target area based upon the receipt of the communication signal via the circuit arranged in the open circuit configuration and the closed circuit configuration respectively. Further, the wireless reader may be configured to generate a notification signal for a user, wherein the notification signal may be indicative of the dry condition or the wet condition detected in the target area.

In another implementation, a method for indicating wet or dry condition to a user is disclosed. The method may comprise positioning at least one sensor within a target area, wherein the at least one sensor may comprise a circuit of a processing unit, a switch and an antenna. The method may further comprise detecting, by the switch, the target area with a dry condition or a wet condition. The method may further comprise arranging, by the switch, the circuit of processing unit, the switch and the antenna in an open circuit configuration or a closed circuit configuration based upon the detection of the dry condition and the wet condition respectively. The method may comprise transmitting, by the antenna, a communication signal to a wireless reader via the circuit arranged in either of the open circuit configuration or the closed circuit configuration. The method may further comprise determining, by the wireless reader, the dry condition or the wet condition in the target area based upon the receipt of the communication signal via the circuit arranged in the open circuit configuration and the closed circuit configuration respectively. Further, the method may comprise generating, by the wireless reader, a notification signal for a user, wherein the notification signal may be indicative of the dry condition or the wet condition detected in the target area.

In yet another implementation, an absorbent article is disclosed. The absorbent article may comprise at least one reusable RFID sensor positioned inside the absorbent article such that the at least one of the reusable RFID sensor is in direct contact with a liquid in the absorbent article. The at least one reusable RFID sensor may further comprise a circuit of an RFID IC, a switch and an antenna. The switch may be configured to detect the absorbent article with a dry condition or a wet condition by sensing the presence or absence of a liquid within the absorbent article. The switch may be configured to arrange the circuit in an open circuit configuration or a closed circuit configuration based upon the detection of the dry condition or the wet condition respectively. The antenna may be configured to transmit a communication signal to an RFID reader wirelessly communicating with the RFID sensor. The communication signal may be transmitted via the circuit arranged in either of the open circuit configuration or the closed circuit configuration. The communication signal received via the circuit arranged in the open circuit configuration or the closed circuit configuration may indicate, to the RFID reader, the dry condition and the wet condition being detected in the absorbent article respectively.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures or characteristics may be combined in any suitable manner in one or more embodiments.

System(s) and method(s) for indicating a wet or dry condition to a user are described. At least one sensor may be positioned within a target area wherein a dry condition or a wet condition is to be detected. The at least one sensor may comprise a circuit of processing unit, a switch and an antenna. In one example, the at least one sensor may be an RFID sensor. Further, the processing unit and the switch may be an RFID IC and wet sensor switch. Hereinafter, the sensor, the processing unit and the switch will be interchangeably referred to as an "RFID sensor", an "RFID IC" and a "wet sensor switch" respectively.

In an aspect, if the RFID sensor is a type A sensor, the RFID IC, the wet sensor switch and the antenna of the RFID sensor may be connected in parallel. Alternatively, if the RFID sensor is a type B sensor, the RFID IC, the wet sensor switch and the antenna of the RFID sensor may be connected in series. The wet sensor switch may detect the target area with the dry condition or the wet condition by sensing a presence/absence of a liquid within the target area. Based upon the detection of the dry condition or the wet condition, the wet sensor switch may act as an "open circuit switch" or a "closed circuit switch" respectively. The wet sensor switch acting as the open circuit switch or the closed circuit switch may arrange the circuit of the RFID IC, the wet sensor switch and the antenna in an open circuit configuration and the closed circuit configuration respectively.

The at least one sensor may be communicatively coupled with a wireless reader. In one example, the wireless reader may be an RFID reader. Hereinafter, the wireless reader will be interchangeably referred to as "RFID reader". In order to communicate with the RFID reader, the sensor may transmit a communication signal, generated by the RFID IC, via the antenna of the sensor. The communication signal may be received by the RFID reader via an antenna within the RFID reader. The communication signal, generated by the RFID IC, has to be routed through the circuit of the RFID IC, the wet sensor switch and the antenna of the sensor. As described above, the circuit may be arranged in either of the open circuit configuration or the closed circuit configuration depending on the dry condition or the wet condition detected by the RFID IC.

If the sensor is a type A sensor with the circuit arranged in the open circuit configuration wherein the RFID IC, the wet sensor switch and the antenna are connected in parallel, the communication signal from the RFID IC may be received by the RFID reader. The RFID reader may determine that since the communication signal is received from the type A sensor with the circuit arranged in the open circuit configuration, the target area is detected with the dry condition. Alternatively, if the sensor is a type B sensor with the circuit arranged in the closed circuit configuration wherein the RFID IC, the wet sensor switch and the antenna are connected in series, the communication signal from the RFID IC may be received by the RFID reader. The RFID reader may determine that since the communication signal is received from the type B sensor with the circuit arranged in the closed circuit configuration, the target area is detected with the wet condition. In some embodiments, both type A sensor and type B sensor may be employed to detect the dry condition or the wet condition in the target area.

The RFID reader may generate a notification signal for a user. The notification signal may be indicative of the dry condition or the wet condition detected in the target area. The notification signal generated by the RFID reader may be in form of an audible signal or a visual signal or a combination thereof. The audible signal and the visual signal may be indicated via a beeper and one or more Light Emitting Diodes (LEDs), respectively, present within the RFID reader. While aspects of described system, method and article for indicating dry/wet condition to a user may be implemented in any number of different computing systems, apparatuses, environments, and/or configurations, the embodiments are described in the context of the following exemplary system.

Figure 1:
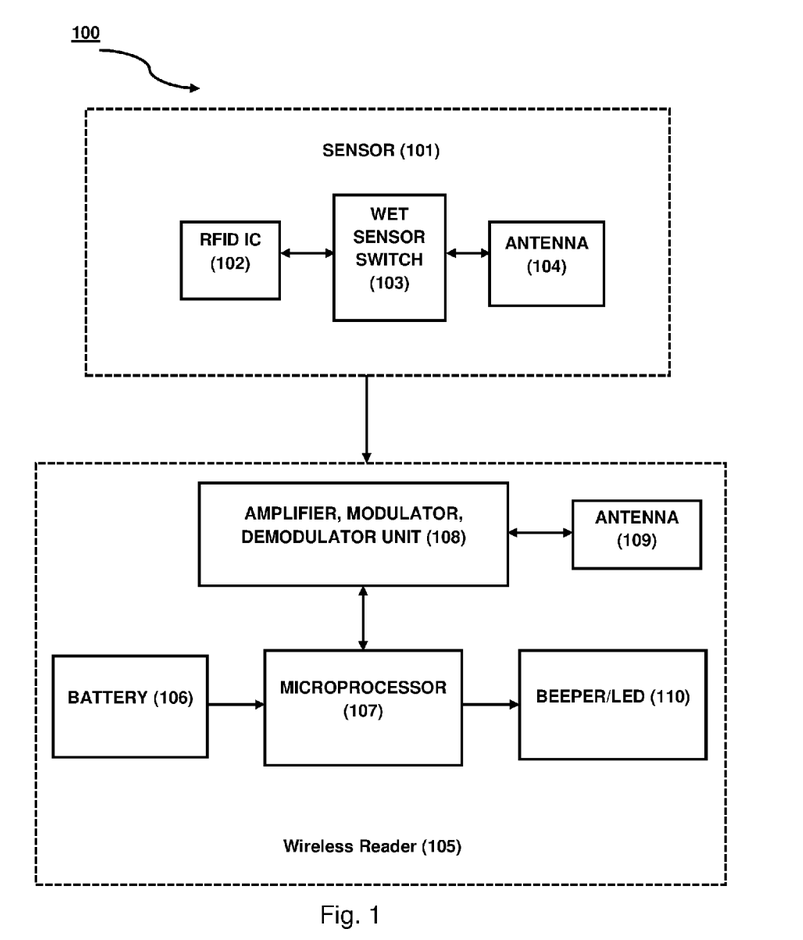
FIG. 1 illustrates a system 100 comprising a sensor 101 and a wireless reader 105 collectively facilitating the indication of a wet or dry condition to a user, in accordance with an embodiment of the present application.

Referring to FIG. 1, a system 100 for indicating wet or dry condition to a user is illustrated, in accordance with an embodiment of the present application. As shown, the system 100 may comprise at least one sensor 101 (hereinafter referred as "sensor 101" or an "RFID sensor 101" interchangeably) and a wireless reader 105 (hereinafter referred as an "RFID reader 105"). In one embodiment, at least one sensor 101 may comprise a processing unit (shown as an "RFID IC 102"), a switch (shown as a "wet sensor switch 103") and an antenna 104. In one embodiment, the RFID IC 102 is a standard Radio Frequency Identification technology wafer. The RFID IC 102 may remove the need of analogue or digital circuit for detecting capacitance, resistance, voltage or current. In one embodiment, the RFID IC 102 may be configured to generate a communication signal to be transmitted to the RFID reader 105 communicatively coupled with the sensor 101. In one embodiment, the sensor 101 may be communicatively coupled with the RFID reader 105 via an RFID communication protocol. The communication signal may be transmitted to the RFID reader 105 via the antenna 104 electrically coupled with the wet sensor switch 103.

As shown in FIG. 1, the RFID reader 105 may further comprise a battery 106, a microprocessor 107, an amplifier, modulator and demodulator (AMD) unit 108 (hereinafter referred as "AMD unit 108"), an antenna 109 and a beeper/LED 110. In an embodiment, the communication signal generated by the RFID IC 102 may be transmitted by the antenna 104 to the RFID reader 105 via an open circuit or a closed circuit formed between the RFID IC 102 and the antenna 104. The open circuit or the closed circuit may be formed between the RFID IC 102 and the antenna 104 by the wet sensor switch 103 based upon sensing of a presence/absence of a liquid within the target area by the wet sensor switch 103.

In an embodiment, the liquid may be water, urine, and the like. It is to be noted that the wet sensor switch 103 is sensitive to resistance of the liquid. The liquid provides conducting path with low resistance for the wet sensor switch 103 and therefore the wet sensor switch 103 may act as a closed switch if there is liquid in the target area. It must be understood that the wet sensor switch 103 acting as the closed switch may form the closed circuit switch between the RFID IC 102 and the antenna 104. In another embodiment, if there is no liquid within the target area, the resistance of the wet sensor switch 103 is high and hence the wet sensor switch 103 may act as an open switch. It must be noted that the wet sensor switch 103, may not consume energy for operation. In one embodiment, the wet sensor switch 103, acting as the open switch or the closed switch, may arrange the circuit of the RFID IC 102, the wet sensor switch 103 and the antenna 104 in the open circuit configuration and the closed circuit configuration respectively.

Figure 2A:
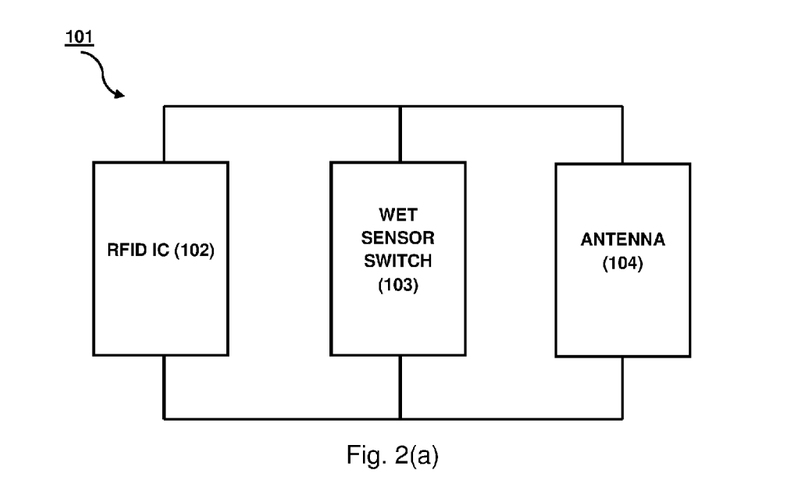
FIG. 2(a) and FIG. 2(b) illustrate the sensor 101 arranged in two circuit configurations, in accordance with an embodiment of the present application.

Referring to FIG. 1, the sensor 101 may be a type A sensor or a type B sensor or a combination thereof. In one embodiment, if the sensor 101 is a type A sensor, the components of the type A sensor 101 including the RFID IC 102, the wet sensor switch 103 and the antenna 104 may be connected in parallel as shown in FIG. 2(*a*). In this embodiment, if the wet sensor switch 103 of the type A sensor 101, positioned within a target area, detects the target area with a dry condition, the wet sensor switch 103 may act as an open switch thereby arranging the circuit in an open circuit configuration. It is to be noted herein that since there is no liquid within the target area, the resistance of the wet sensor switch 103 is high and therefore the wet sensor switch 103 act as an open switch. Since, the components of the type A sensor 101 are connected in parallel, the communication signal generated by the RFID IC 102 may be transmitted to the RFID reader 105 via the open circuit arrangement of the RFID IC 102, the wet sensor switch 103 and the antenna 104.

On the contrary, if the wet sensor switch 103 of the type A sensor 101 detects the target area with a wet condition, the wet sensor switch 103 may act as a closed switch thereby arranging the circuit in a closed circuit configuration. It is to be noted herein that since there is a liquid within the target area, the wet sensor switch 103 being resistant to the liquid, the resistance of the wet sensor switch 103 is low. This is because, the liquid provides conductive path to the wet sensor switch 103 and therefore the wet sensor switch 103 acts as the closed switch. Since, the components of the type A sensor 101 are connected in parallel with the circuit arranged in the closed circuit configuration, the communication signal generated by the RFID IC 102 may be failed to be transmitted to the RFID reader 105. Therefore, the type A sensor 101 may communicate with the RFID reader 105 only when the dry condition is detected by the wet sensor switch 103 within the target area. Thus, the receipt of the communication signal from the type A sensor 101 enables the RFID reader 105 to determine that the dry condition is being detected in the target area. Alternatively, if the RFID reader 105 fails to receive the communication signal from the type A sensor 101, the RFID reader 105 may determine that the wet condition is being detected in the target area.

Figure 2B:
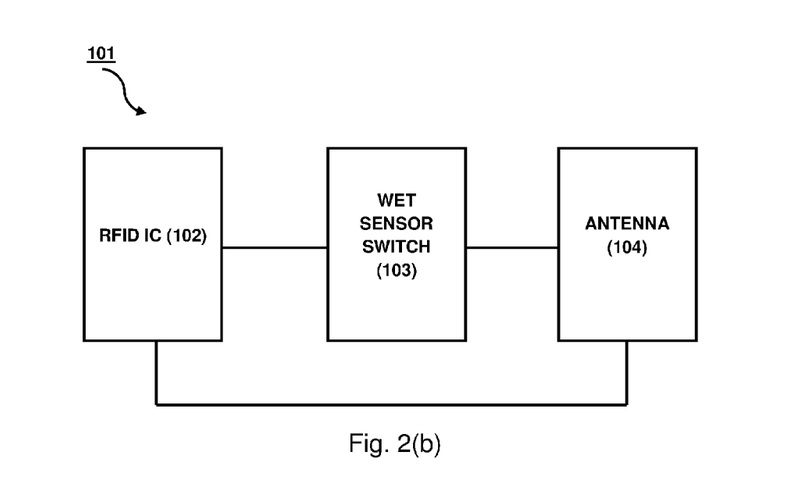

In an another embodiment, if the sensor 101 is a type B sensor, the components of the type B sensor 101 including the RFID IC 102, the wet sensor switch 103 and the antenna 104 may be connected in series as shown in FIG. 2(*b*). In this embodiment, if the wet sensor switch 103 of the type B sensor 101, positioned within a target area, detects the target area with a wet condition, the wet sensor switch 103 may act as a closed switch thereby arranging the circuit in a closed circuit configuration. It is to be noted herein that since there is a liquid within the target area, the wet sensor switch 103 being resistant to the liquid, the resistance of the wet sensor switch 103 is low. This is because, the liquid provides conductive path to the sensor switch 103 and therefore the wet sensor switch 103 may act as the closed switch. Since, the components of the type B sensor 101 are connected in series, the communication signal generated by the RFID IC 102 may be transmitted to the RFID reader 105 via the closed circuit arrangement of the RFID IC 102, the wet sensor switch 103 and the antenna 104.

On the contrary, if the target area is detected with a dry condition by the wet sensor switch 103 of the type B sensor 101, the wet sensor switch 103 may act as an open switch thereby arranging the circuit in an open circuit configuration. It is to be noted herein that since there is no liquid within the target area, the resistance of the wet sensor switch 103 is high and therefore the wet sensor switch 103 acts as an open switch. Since, the components of the type B sensor 101 are connected in series with the circuit arranged in the open circuit configuration, the communication signal generated by the RFID IC 102 may be failed to be transmitted to the RFID reader 105. Therefore, the type B sensor 101 may communicate with the RFID reader 105 only when the wet condition is detected by the wet sensor switch 103 within the target area. Thus, the receipt of the communication signal from the type B sensor 101 enables the RFID reader 105 to determine that the wet condition is being detected in the target area. Alternatively, if the RFID reader 105 fails to receive the communication signal from the type B sensor 101, the RFID reader 105 may determine that the dry condition is being detected in the target area.

In an embodiment, the sensor 101 may comprise a combination of a type A sensor and a type B sensor positioned within the target area. In this embodiment, if the target area is detected with the dry condition, then the type A sensor may communicate with the RFID reader 105. Whereas, if the target area is detected with the wet condition, the type B sensor may communicate with the RFID reader 105. Therefore, irrespective of the condition of the target area, one of the two sensors (type A sensor and type B sensor) embedded within the sensor 101 is always in communication with the RFID reader 105 thereby indicating the dry condition or the wet condition to the RFID reader 105.

The RFID reader 105 may determine the dry condition or the wet condition in the target area based upon the communication signal received from the type A sensor and the type B sensor respectively. In one embodiment, the RFID reader 105 may receive the communication signal via the antenna 109, of the RFID reader 105, capable of absorbing and emitting radio waves. In one embodiment, the communication signal received by the antenna 109 may be fed to the AMD unit 108. The AMD unit 108 may convert the communication signal into an appropriate signal to be used by the microprocessor 107 for processing and analysis of the communication signal information received from the sensor 101. The battery 106 may supply power to the components of the RFID reader 105 including the microprocessor 107, the AMD unit 108, the antenna 109 and the beeper/LED 110.

The microprocessor 107 of the RIFD reader 105 may store a plurality of programmed instructions within an internal memory of the microprocessor 107 or an external memory (not shown) coupled with the microprocessor 107. The plurality of programmed instructions may include routines, programs, objects, components, data structures, etc., which perform particular tasks or implement particular abstract data types. Among other capabilities, the microprocessor 107 may be configured to fetch and execute plurality of programmed instructions. The microprocessor 107 may execute one or more programmed instructions for analyzing Radio Frequency Identification (RFID) technology requirements and the communication signal information received from the sensor 101. In one embodiment, the microprocessor 107 may further execute one or more programmed instructions for matching the communication signal information with preprogrammed data stored within the microprocessor 107. The preprogrammed data may indicate the dry condition or the wet condition being detected within the target area based upon receipt of the communication signal from the type A sensor and type B sensor respectively. The RFID reader 105 may detect the type of the sensor 101 as one of the type A sensor and the type B sensor by matching the communication signal information with the preprogrammed data and accordingly determine the dry condition or the wet condition being detected within the target area.

Figure 3:
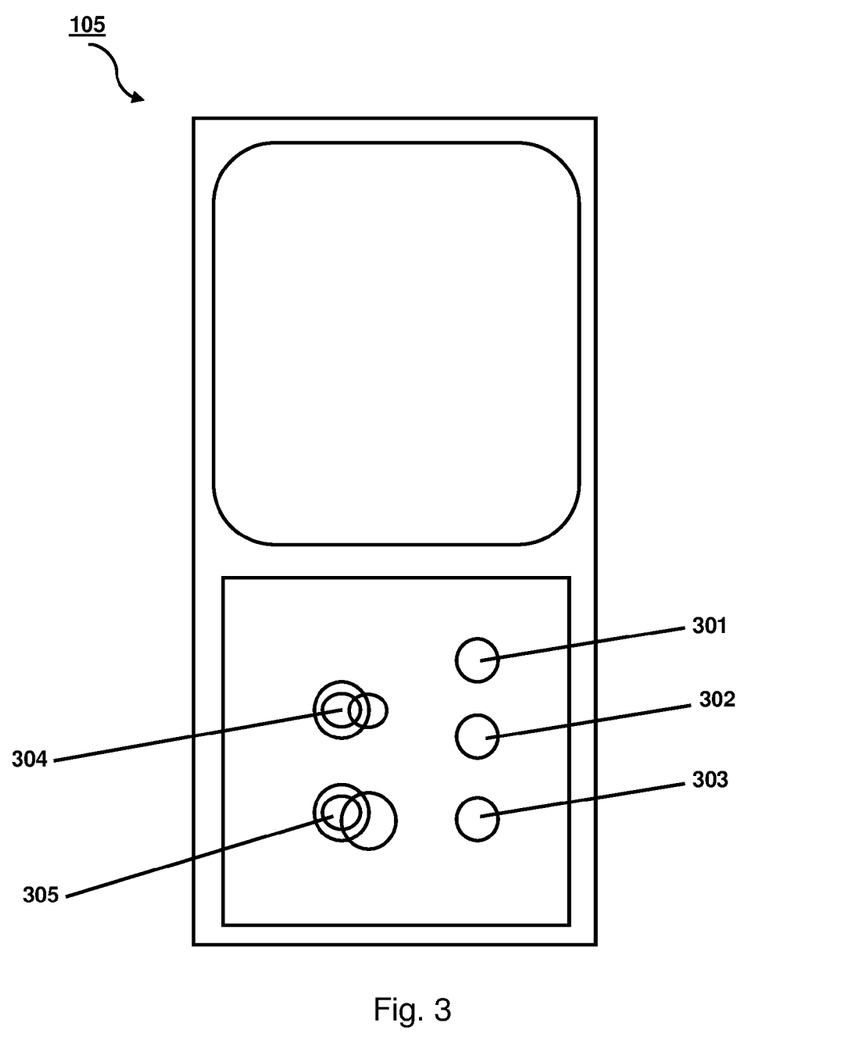
FIG. 3 illustrates the wireless reader 105, in accordance with an embodiment of the present application.

Based upon the determination of the dry condition or the wet condition, the microprocessor 107 may further execute one or more programmed instructions for triggering beeper/ LEDs 110 to generate a notification signal for a user in order to notify the user about the wet/dry condition being detected in the target area. In an embodiment, the microprocessor 107 may provide a modulated signal for communicating with the sensor 101 and providing required energy for the RFID chips. FIG. 3 illustrates the RFID reader 105, in accordance with an embodiment of the present application. As shown in FIG. 3, the RFID reader 105 may comprise a plurality of Light Emitting Diodes (LEDs). The plurality of LEDs may comprise a dry LED 301, a wet LED 302 and a status LED 303. Further, the RFID reader 105 may comprise a power button 304 and a learn button 305. The power button 304 may be used to power ON/OFF the RFID reader 105.

In one embodiment, if the target area is detected with the dry condition, the user may be indicated with the dry condition being detected in the target area by flashing the dry LED 301 (visual indication) and triggering a beep signal (audio indication) using a beeper (not shown). In another embodiment, if the target area is detected with the wet condition, the user may be indicated with the wet condition being detected in the target area by flashing the wet LED 302 (visual indication) and triggering a beep signal (audio indication) using the beeper.

In one embodiment, the status LED 303 may indicate the status of the RFID reader 105. In one embodiment, the status LED 303 may be flashed to indicate the RFID reader 105 is in "standby mode". Further, the status LED 303 may be flashed and a beep may be generated by the beeper to indicate the RFID reader is in the standby mode with low battery. The RFID reader 105 may be in "OFF mode" when the dry LED 301, the wet LED 302 and the status LED 303 are OFF and are not flashing. In one embodiment, the RFID reader 105 may switch from the "standby mode" to the "OFF mode" when the sensor 101 fails to detect the dry or wet condition within the target area for a predefined time interval of 30 seconds.

Figure 4:
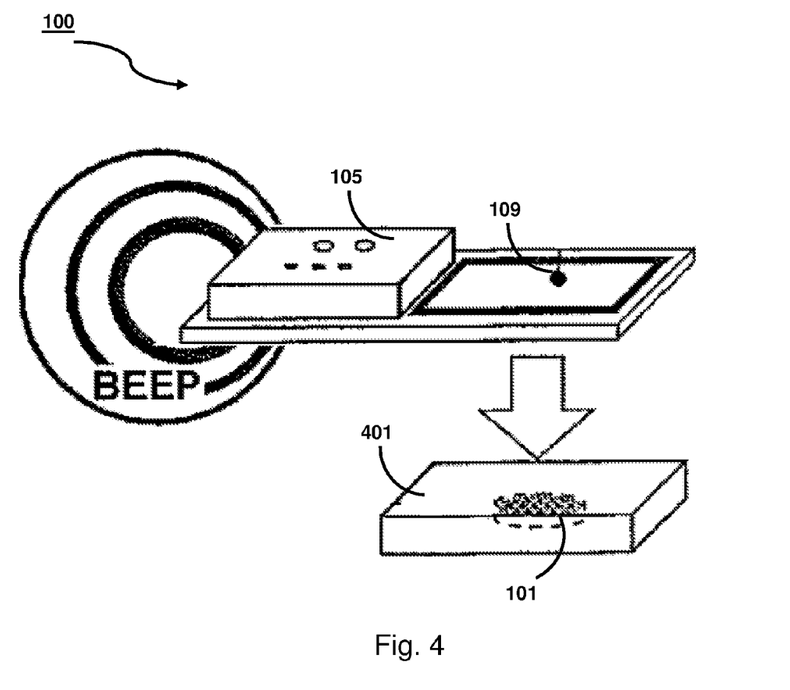
FIG. 4 illustrates the working of the system 100, in accordance with an embodiment of the present application.

Referring to FIG. 4, an exemplary implementation of the system 100 for detecting wet or dry condition is illustrated. In this implementation, the sensor 101 is positioned within a cloth 401. In one embodiment, if the cloth is a dry cloth with no liquid therein, the receipt of the communication signal from the sensor 101 (e.g. type A sensor in this case), by the antenna 109 of the RFID reader 105, may trigger the flashing of the dry LED 301 (shown in FIG. 3) as-well-as generating a beep within the predefined time interval of thirty seconds. In another embodiment, if the cloth is a wet cloth with liquid therein, the receipt of the communication signal, from the sensor 101 (e.g. type B sensor in this case), by the antenna 109 of the RFID reader 105 may trigger the flashing of the dry LED 301 (shown in FIG. 3) as-well-as generating a beep within the predefined time interval of thirty seconds.

The RFID reader 105 may be adapted to detect the type of sensor 101 by matching the sensor 101 to the RFID reader 105. In order to match the sensor 101 to the RFID reader 105, the sensor 101 may be positioned on the dry cloth. The learn button 305 may be pressed and held for a predefined time interval of two seconds until the dry LED 301 is flashed. Further, the RFID reader 105 may be moved closer to the sensor 101 until the dry LED 301 flashes and beeps for a predefined time interval of one second. The learn button 305 may be pressed again and the wet LED 302 is turned "ON". The sensor 101 may be placed on a wet cloth. Further, the RFID reader 105 may be moved closer to the sensor 101 until the wet LED 302 flashes and beeps for predefined time interval of one second. In this manner, the sensor 101 may be matched to the RFID reader 105 for detection of the sensor by the RFID reader 105.

Figure 5:
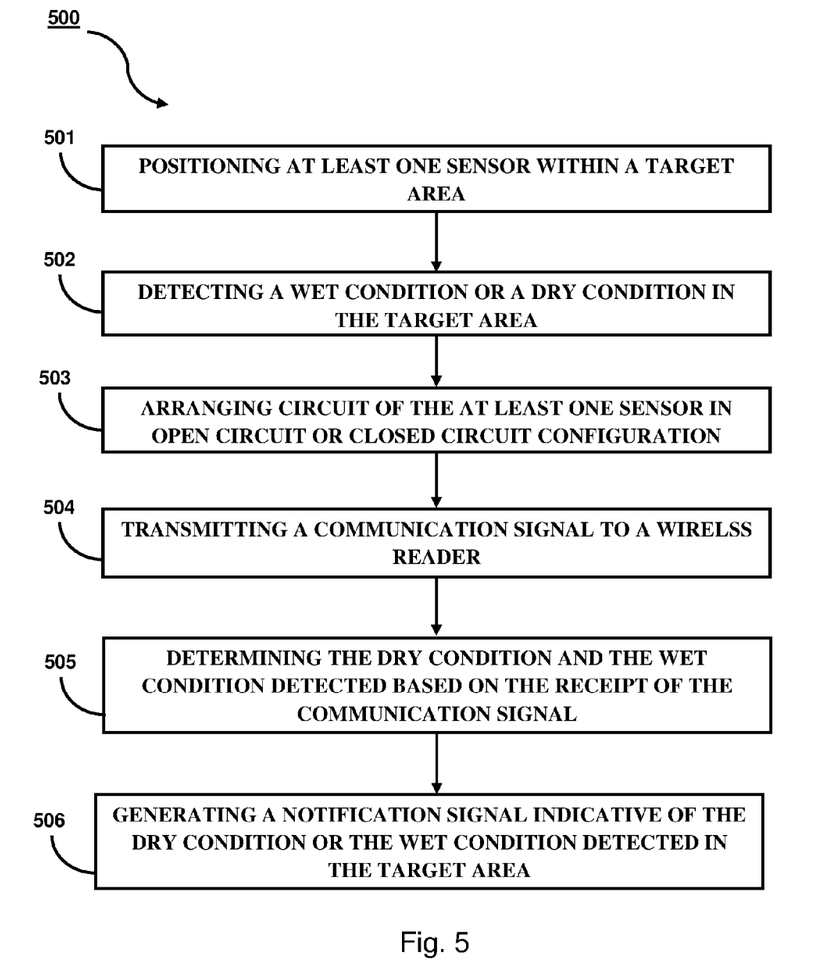
FIG. 5 illustrates a method 500 for indicating dry or wet condition to a user, in accordance with an embodiment of the present application.

Now referring to FIG. 5, a method 500 for indicating wet or dry condition to a user is illustrated, in accordance with the embodiment of the present application. The order in which the method 500 is described is not intended to be construed as a limitation, and any number of the described method blocks can be combined in any order to implement the method 500 or alternate methods. Furthermore, the method 500 may be implemented in any suitable hardware, software, firmware, or combination thereof. However, for ease of explanation, in the embodiments described below, the method 500 may be considered to be implemented in the above described system 100.

As shown in FIG. 5, at block 501, at least one sensor 101 may be positioned within a target area wherein the wet/dry condition is being detected. In one embodiment, the at least sensor 101 may comprise a circuit of a processing unit 102, a switch 103 and an antenna 104. The at least one sensor 101 may be communicatively coupled with the wireless reader 105.

At block 502, the target area may be detected with a dry condition or a wet condition. In one implementation, the target area may be detected with the dry condition or the wet condition by the switch 103 of the at least one sensor 101.

At block 503, the circuit of the at least one sensor 101 may be arranged in either of an open circuit configuration or a closed circuit configuration based upon the detection of the dry condition or the wet condition, respectively, in the target area. In one implementation, the circuit of the at least one sensor 101 may be arranged in either of the open circuit configuration or the closed circuit configuration by the switch 103 of the at least one sensor 101.

At block 504, a communication signal may be transmitted to the wireless reader 105 via the circuit arranged in either of the open circuit configuration or the closed circuit configuration. In an embodiment, the communication signal may be generated by the processing unit. In one implementation, the communication signal may be transmitted to the wireless reader by the antenna 104 of the at least one sensor 101.

At block 505, the wireless reader 105 may determine the dry condition or the wet condition detected in the target area based upon the receipt of the communication signal via the circuit arranged in the open circuit configuration and the closed circuit configuration respectively. In one implementation, the wireless reader 105 may receive the communication signal via the antenna 109 present within the wireless reader 105.

At block 506, a notification signal for a user may be generated by the wireless reader 105. The notification signal may be indicative of the dry condition or the wet condition detected in the target area. In one implementation, the notification signal may be generated via a beeper or LEDs or combinations thereof. The beeper or the LEDs may be present within the wireless reader 105.

In one exemplary embodiment, the system 100 may be implemented in an absorbent material such as a diaper used by children and adults. The sensor 101 (either type A sensor or type B sensor or a combination thereof) may be positioned inside the diaper such that the at least one of the reusable RFID sensor is in direct contact with a liquid in the diaper. The sensor 101 may be a reusable RFID sensor capable of being reused after the diaper is disposed. The RFID sensor 101 may comprise an RFID IC 102, a wet sensor switch 103 and an antenna 104. The wet sensor switch 103 may detect the diaper with a dry condition or a wet condition by sensing the presence/absence of a liquid within the diaper. The wet sensor switch 103 may arrange the circuit in an open circuit configuration or a closed circuit configuration based upon the detection of the dry condition or the wet condition respectively. The antenna 104 may transmit a communication signal generated by the RFID IC 102 to the RFID reader 105 wirelessly communicating with the RFID sensor 101. The RFID reader 105 may receive the communication signal via the circuit arranged in the open circuit configuration or the closed circuit configuration. The communication signal received via the circuit arranged in the open circuit configuration or the closed circuit configuration may indicate the dry condition and the wet condition being detected within the diaper, respectively, to the RFID reader 105. The RFID reader 105 may generate a notification signal for a user, wherein the notification signal may be indicative of the dry condition or the wet condition detected in the diaper. The notification signal may be generated in form of an audible signal or a visual signal or a combination thereof. The audible signal and the visual signal may indicate to the user via a beeper and one or more Light Emitting Diodes (LEDs), respectively, present within the RFID reader 105.

Exemplary embodiments discussed above may provide certain advantages. Though not required to practice aspects of the application, these advantages may include those provided by the following features.

Some embodiments of the present application enable system and method providing sensors deployed in absorbent materials such as a diaper for detecting dry/wet conditions within the diaper, wherein such sensors may be further reused in a fresh diaper or other applications after the diaper is disposed.

Some embodiments of the present application enable system and method provisioning placement of the two different type of sensors (type A sensor and type B sensor) within the target area such that one of the two sensors are configured to detect the dry condition in the target area, and wherein the other sensor is configured to detect the wet condition in the target area.

Although implementations for systems, articles and methods for indicating wet or dry condition to a user have been described in language specific to structural features and/or methods, it is to be understood that the appended claims are not necessarily limited to the specific features or methods described. Rather, the specific features and methods are disclosed as examples of implementations for indicating wet or dry condition to a user.

What is claimed is:

1. A system for indicating wet or dry condition to a user, the system comprising:
 a first sensor and a second sensor positioned within a target area of an absorbent article; and
 an Radio-frequency identification (RFID) reader;
 wherein the first sensor comprises
  a first circuit comprising a first RFID IC, a first switch and a first antenna connected in parallel, the first switch acting as a closed switch if there is liquid within the target area and an open switch if there is no liquid within the target area,
  the first switch being configured to detect the target area with a dry condition, and arrange the first circuit in an open circuit configuration based upon the detection of the dry condition,
  the first RFID IC being configured to generate a first communication signal when the first circuit is in the open circuit configuration, and
  the first antenna being configured to transmit the first communication signal to the RFID reader;
 the second sensor comprises
  a second circuit comprising a second RFID IC, a second switch and a second antenna connected in series, the second switch acting as a closed switch if there is liquid within the target area and an open switch if there is no liquid within the target area,
  the second switch being configured to detect the target area with a wet condition, and arrange the second circuit in a closed circuit configuration based upon the detection of the wet condition,
  the second RFID IC being configured to generate a second communication signal when the second circuit is in the closed circuit configuration, and
  the second antenna being configured to transmit the second communication signal to the RFID reader;
 the RFID reader is configured to receive the first or second communication signal, determine the target area is in the dry condition or the wet condition, and generate a notification signal for a user, the notification signal being indicative of the dry condition or the wet condition detected in the target area.

2. The system of claim 1, wherein the notification signal generated by the RFID reader is in form of an audible signal or a visual signal or a combination thereof.

3. The system of claim 2, wherein the audible signal and the visual signal is indicated via a beeper and one or more Light Emitting Diodes (LEDs) respectively, wherein the beeper and the one or more LEDs are present within the RFID reader.

4. A method for indicating wet or dry condition to a user, the method comprising:
 positioning a first sensor and a second sensor within a target area of an absorbent article, wherein the first sensor comprises
  a first circuit comprising a first RFID IC, a first switch and a first antenna connected in parallel, the first switch acting as a closed switch if there is liquid within the target area and an open switch if there is no liquid within the target area,
  the first switch being configured to detect the target area with a dry condition, and arrange the first circuit in an open circuit configuration based upon the detection of the dry condition,
  the first RFID IC being configured to generate a first communication signal when the first circuit is in the open circuit configuration, and the first antenna being configured to transmit the first communication signal to an Radio-frequency identification (RFID) reader;
 the second sensor comprises
  a second circuit comprising a second RFID IC, a second switch and a second antenna connected in series, the second switch acting as a closed switch if there is liquid within the target area and an open switch if there is no liquid within the target area, the second switch being configured to detect the target area with a wet condition, and arrange the second circuit in a closed circuit configuration based upon the detection of the wet condition, the second RFID IC being configured to generate a second communication signal when the second circuit is in the closed circuit configuration, and the second antenna being configured to transmit the second communication signal to the RFID reader;

detecting, by the first sensor and the second sensor, the target area with the dry condition or the wet condition;

receiving, by the RFID reader, the first or second communication signal, determining the target area is in the dry condition or the wet condition, and generating a notification signal for a user, the notification signal being indicative of the dry condition or the wet condition detected in the target area.

5. An absorbent article, comprising:

a first reusable sensor and a second reusable sensor positioned inside the absorbent article such that the first reusable sensor and the second reusable sensor are in direct contact with a liquid in the absorbent article, wherein the first sensor comprises a first circuit comprising a first RFID IC, a first switch and a first antenna connected in parallel, the first switch acting as a closed switch if there is liquid within the target area and an open switch if there is no liquid within the target area, the first switch being configured to detect the target area with a dry condition, and arrange the first circuit in an open circuit configuration based upon the detection of the dry condition, the first RFID IC being configured to generate a first communication signal when the first circuit is in the open circuit configuration, and the first antenna being configured to transmit the first communication signal to an Radio-frequency identification (RFID) reader;

the second sensor comprises a second circuit comprising a second RFID IC, a second switch and a second antenna connected in series, the second switch acting as a closed switch if there is liquid within the target area and an open switch if there is no liquid within the target area, the second switch being configured to detect the target area with a wet condition, and arrange the second circuit in a closed circuit configuration based upon the detection of the wet condition, the second RFID IC being configured to generate a second communication signal when the second circuit is in the closed circuit configuration, and the second antenna being configured to transmit the second communication signal to the RFID reader.

* * * * *